United States Patent [19]

Rothman et al.

[11] Patent Number: 4,652,530
[45] Date of Patent: Mar. 24, 1987

[54] MONITORING METHOD FOR ISOTHIAZOLONES IN AQUEOUS SYSTEMS

[75] Inventors: Alan M. Rothman, Jenkintown; Charles C. Crabb, Green Lane, both of Pa.

[73] Assignee: Rohm and Haas Company, Philadelphia, Pa.

[21] Appl. No.: 754,546

[22] Filed: Jul. 15, 1985

[51] Int. Cl.$^4$ .................. G01N 1/18; G01N 31/02
[52] U.S. Cl. .................................. 436/92; 436/178; 436/904
[58] Field of Search ............... 436/92, 106, 119, 169, 436/178, 904

[56] References Cited

U.S. PATENT DOCUMENTS 3,975,155  8/1976  Geyer .................................. 436/178
4,110,378  8/1978  Geyer .............................. 502/402 X

OTHER PUBLICATIONS

"Rapid Visual Estimation and Spectrophotometric Determination of Tannin Content of Sorghum Grain", *J. Agric. Food Chem.*, 25 (6), pp. 1268–1273.
"Analysis of Total Phenols Using the Prussian Blue Method," *J. Agric. Food Chem.*, 28, pp. 1236–1238.
"Iron Compounds," Encyclopedia of Chemical Technology, 13, (1981), pp. 764–771, 788.

*Primary Examiner*—Barry S. Richman
*Assistant Examiner*—Jill Johnston
*Attorney, Agent, or Firm*—Marc S. Adler

[57] ABSTRACT

A quantitative, sensitive method for monitoring low concentrations of isothiazolones in aqueous systems is provided. The method involves the adsorption of the isothiazolones on a suitable adsorbent, the desorption of the adsorbed isothiazolones, the breaking of the isothiazolone ring and the formation of a blue complex by the reaction of the broken isothiazolone ring with ferric chloride and potassium ferricyanide. The concentration of the isothiazolones is then determined by conventional colorimetric techniques.

8 Claims, No Drawings

MONITORING METHOD FOR ISOTHIAZOLONES IN AQUEOUS SYSTEMS

BACKGROUND OF THE INVENTION

This invention relates to a quantitative, colorimetric method for determining the concentration of isothiazolones in aqueous systems, and more particularly to a highly sensitive monitoring method for determining low concentrations of isothiazolones in aqueous systems, such as cooling tower and swimming pool water, containing other biocides, additives and contaminants.

FIELD OF THE INVENTION

Isothiazolones, as defined herein, refer to substituted and unsubstituted 3-isothiazolones and mixtures having the structural formula:

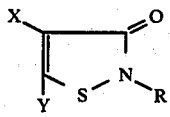

where
R is hydrogen, an unsubstituted or substituted alkyl group of 1 to 10 carbon atoms, an unsubstituted or substituted cycloalkyl group of 3 to 8 carbon atoms, an unsubstituted or substituted aralkyl group of up to 10 carbon atoms, or an unsubstituted or substituted aryl group of up to 10 carbon atoms;
X and Y are independently a hydrogen atom, a halogen atom or a ($C_1$–$C_4$) alkyl group or when taken together form a substituted or unsubstituted benzene ring to give a compound of the formula:

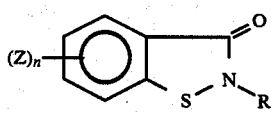

where Z is a ($C_1$–$C_4$) alkyl group, a ($C_1$–$C_4$) alkoxyl group, a cyano group, a nitrogen group, or a halogen group; and
n is a integer of from zero to two.

Some of the isothiazolones present in aqueous systems may be in the form of complexed divalent salts such as magnesium or calcium.

Isothiazolones, marketed by Rohm and Haas Company under the trademark Kathon ®, are antibacterial agents or biocides which are widely used in a variety of aqueous and non-aqueous systems. For example, isothiazolones are useful as algaecides in swimming pools and as slimicides in cooling tower water.

Attempts have been made to develop a rapid, reliable and sensitive method for determining the concentration of isothiazolones in aqueous systems for use in field applications without the need to employ sophisticated and expensive gas chromatographic, liquid chromatographic (HPLC) or ultraviolet spectrophotometric techniques. These prior field monitoring techniques have been found to be less than satisfactory because of the susceptibility of the techniques to positive and negative interferences caused by additives and ionic impurities commonly found in aqueous systems, such as cooling tower water; and because of the difficulty in obtaining a high degree of sensitivity for measuring low concentrations of isothiazolones. Various additives are typically added to recirculating cooling tower water to prevent or inhibit the precipitation of hardness ions, to disperse scale, and to combat corrosion. For example, polyacrylates, phosphates, phosphonates, iron, zinc, tin and other metals are commonly found in cooling tower water as well as suspended particulate materials such as clay and silt.

U.S. Pat. Nos. 3,975,155 and 4,110,378 are directed to a prior colormetric determination method for isothiazolones in aqueous and nonaqueous systems. This method as described in U.S. Pat. No. 3,975,155 involves the separation of the isothiazolones from the medium by adsorption on a suitable support such as a packed column containing a polymeric macroreticular adsorbent. The adsorbed isothiazolones are then reacted with a metal hydride, such as sodium borohydride, to reductively cleave the isothiazolone ring forming a thiol. The thiol is then eluted from the column using a protic solvent such as methanol. The colorimetric measurement is conducted by adding of a yellow color forming agent such as 5,5'-dithio-bis(2-nitrobenzoic acid) to the eluted thiol. The sensitivity of this colorimetric technique, utilizing the yellow color, is not sufficiently high for effective monitoring of isothiazolone concentrations on the order of one part per million and less.

Another colorimetric technique for monitoring isothiazolones was published in 1981. This method involved the extraction of isothiazolones from a sodium chloride-saturated aqueous phase into ethyl acetate. Extraction of the isothiazolones with ethyl acetate also results in a yellow color susceptible to visual comparison with a standard. This technique suffers from difficulties in phase separation during the extraction and from interferences which may or may not be eliminated with a pre-cleaning step.

Colorimetric techniques, that utilize a blue color capable of improved sensitivity at low concentrations, have been developed for measuring the concentration of polyphenols in aqueous streams. *Rapid Visual Estimation and Sepctrophotometric Determination of Tanning Content of Sorghum Grain,* Price and Butler, J. Agric. Food Chem., Vol. 25, No. 6, pages 1268–1271, describes a colorimetric method for the estimation of tannin concentration in sorghum grains. When the tannins or polyphenols are reacted with an aqueous solution containing $FeCl_3$ and $K_3Fe(CN)_6$, a Prussian blue complex is formed. The color can be visually correlated with concentration or colorimetrically evaluated by measuring absorbance at about 720 nanometers. The article shows that the slope of the absorbance versus concentration curve is sufficiently high at low concentrations to yield good sensitivity for the tannin concentration. *Analysis of Total Phenols Using the Prussian Blue Method,* Budini, Tonelli and Girotti, Jr. Agric. Food Chem., 1980, 28, 1236–1238, describes the use of the Prussian blue complex with a spectrophotometer for the determination of the concentration of phenolics in vegetables and fruits, especially strawberries. This technique permits one to judge the ripeness of strawberries as the total phenol content of a strawberry decreases as ripeness increases. Budini et al states that this method is about 20 times as sensitive as a conventional acidified vanillin method. While this method is described as being an improvement over the Price method, it has problems with ascorbic acid interference.

Although the Prussian blue method has been shown to be useful with polyphenols in fruits, vegetables and grain, these references do not teach or suggest that a simple colorimetric method utilizing the blue color complex can be used for monitoring low concentrations of non-phenolics, such as isothiazolones, in aqueous systems containing other ions and materials.

At the present time, therefore, low concentrations of isothiazolones in aqueous systems cannot be effectively monitored in the field without the use of a gas chromatograph, high pressure liquid chromatograph or spectrophotometer. A simple, fast and sensitive method is, therefore, desired by operators of cooling towers and other aqueous systems to enable them to make economical decisions in the field concerning the timing and need for the addition of isothiazolones to their system.

It is, therefore, an object of the present invention to provide a fast, reproducible, simple and sensitive method for monitoring low concentrations of isothiazolones in aqueous systems, without the use of sophisticated and expensive instruments, so that the concentration of isothiazolones can be monitored in the field.

It is an object of the present invention to provide such a method that is specifically adapted for use with cooling waters containing ionic impurities.

SUMMARY OF THE INVENTION

We have found that the above objectives can be realized by a novel colorimetric monitoring method comprising pretreating the aqueous system containing isothiazolones at elevated pH, adsorbing the isothiazolones from the pretreated system onto a non-polar adsorbent, desorbing the isothiazolones from said adsorbent, treating the desorbed isothiazolones with a base to break the isothiazolone ring, reacting the base treated isothiazolones with ferric chloride and potassium ferricyanide to produce a blue complex, and colorimetrically correlating the blue color formed with the concentration of the isothiazolone in the aqueous system.

This method is fast, simple, reproducible, and sensitive to the presence of isothiazolones in aqueous systems at concentrations of about one part per million and lower. The method is particularly useful for monitoring the concentration of isothiazolones in cooling tower waters.

DETAILED DESCRIPTION OF THE INVENTION

The method of this invention is directed to the quantitative determination of low levels of isothiazolones in aqueous systems, and particularly for monitoring isothiazolones in cooling tower waters at concentrations of from about 0.1 to about 20 parts per million.

The method of the invention involves four basic steps:

(1) pretreatment of the aqueous sample containing isothiazolones to eliminate interferences and to enhance adsorption;

(2) adsorption of the isothiazolones in the pretreated sample using a suitable non-polar adsorbent;

(3) desorbing the adsorbed isothiazolone from the adsorbent;

(4) breaking the isothiazolone ring using a base; and (5) forming a blue complex capable of highly sensitive colorimetric analysis by adding ferric chloride and potassium ferricyanide to the sample containing the broken ring-isothiazolones.

We have found that a pretreatment step is necessary to increase the retention of the isothiazolone in the sample onto a suitable nonpolar adsorbent and to remove ions and other materials that could cause positive and negative interferences. When cooling tower water samples from commercial cooling towers were evaluated, we found that without a pretreatment step the method did not correlate well with high pressure liquid chromatographic analytical results. We believe that these differences were caused by positive and negative interferences caused by the presence of phosphonates, sodium tripolyphosphate, mercaptans or sulfides in the aqueous system. When the pH of the aqueous samples containing the isothiazolones was raised, before adsorption, hereinafter referred to as "pretreatment", to about pH 10, we found that the results of the method more closely matched the high pressure liquid chromatography results. Increasing the pH much above pH 10 may adversely affect the cartridge and/or cleave the isothiazolone ring, while lowering the pH much below pH 10 has an adverse affect on the adsorption of the isothiazolones onto the adsorbent. We have theorized that the pretreatment step is useful to increase the retention of the isothiazolones on the adsorbent while removing interfering compounds. It is believed that the pretreatment may convert water soluble isothiazolone complexed divalent salts to water insoluble inorganic hydroxides which precipitate and converts the isothiazolones to the "free base form" which is more nonpolar and adsorbs better onto the adsorbent. The results of the method with and without the pretreatment step utilizing Kathon ® 886 are presented in Table 1.

TABLE 1

| | Concentration (ppm) of Isothiazolones in Commercial Waters | | | |
|---|---|---|---|---|
| | No Pretreatment | | Pretreatment | |
| Sample | Color Test (ppm) | HPLC (ppm) | Color Test (ppm) | HPLC (ppm) |
| 1 | 4 | <0.4 | (g) | (g) |
| 2 | 6 | <0.4 | (g) | (g) |
| 3 | <0.1 | <0.4 | <0.2 | <0.4 |
| 4(a) | — | — | 1.1 | 1.1 |
| 5 | 0.7 | 1.1 | — | — |
| 6 | <0.1 | <0.4 | <0.2 | <0.4 |
| 7(a) | — | — | 1.2 | 0.9 |
| 8(c) | 11 | <0.4 | 5.4 | <0.4 |
| 9(b)(c) | — | — | 7.6 | 0.8–1.0 |
| 10(c) | 20 | 10 | 12.1 | 10.0 |
| 11(b)(c) | — | — | 14.0 | 10.5 |
| 12 | 0.3 | <0.4 | <0.2 | <0.4 |
| 13(d) | — | — | 0.4 | 0.5 |
| 14(e) | — | — | 0.9 | 0.9–1.1 |
| 15 | <0.3 | — | <0.2 | <0.2 |
| 16(d) | — | — | 0.4 | 0.6 |
| 17 | neg | — | <0.2 | <0.2 |
| 18(a) | — | — | 0.8 | 0.9 |
| 19 | 4.2 | 4.7 | 4.0 | 4.2 |
| 20(b)(f) | — | — | 5.2 | 6.3 |
| 21 | 1.5 | <0.4 | <0.2 | <0.2 |
| 22(a) | — | — | 0.8 | 0.9 |
| 23 | 2.1 | <0.4 | <0.2 | <0.2 |
| 24(a) | — | — | 0.8 | 0.9 |
| 25 | 2.1 | <0.4 | <0.2 | <0.2 |
| 26(a) | — | — | 1.0 | 0.7 |

(a)Same as previous sample, but with addition of isothiazolone until the concentration of isothiazolone reached 1 ppm.
(b)same as previous sample, but with addition of isothiazolone until the concentration of isothiazolone reached 1 ppm.
(c)Results obtained were not consistent with the results obtained with other commercial cooling tower waters.
(d)same as previous sample, but with addition of isothiazolone until the concentration of isothiazolone reached 0.5 ppm.
(e)same as sample 12, but with the addition of isothiazolone until the concentration of isothiazolone reached 1 ppm.
(f)Test results by color test method not perfectly additive; should have resulted in a total of 6 ppm isothiazolone.

In addition to pretreating the sample by adjusting its pH to about pH 10, we have also found that the method of the invention can be improved by filtering the pretreated aqueous sample to remove particulates and precipitates. The pretreated isothiazolone-containing aqueous sample is preferably filtered as by a 5 micrometer Acrodisc ® filter to remove particulates and precipitates prior to the pretreated samples introduction to the adsorbent.

The isothiazolones in the pretreated aqueous sample of known volume are then adsorbed onto a suitable nonpolar adsorbent of known weight. The adsorbent must have the capability and capacity to selectively adsorb small concentrations of isothiazolones while allowing the adsorbed materials to be easily desorbed therefrom by the use of a small quantity of a noninterfering displacement fluid. In addition, the adsorbent and displacement fluid must not interfere with the chemical structure of the isothiazolones. The adsorbents which have been found to be suitable for the method of this invention include nonpolar, bonded phase, silica gels including octadecyl silane bonded to silca gel. The preferred silica gel adsorbent is Sep-Pak ® C-18 manufactured by Waters Associates. Other suitable silica gel adsorbents include Baker-10 octadecyl manufactured by J. T. Baker Company and Bond Elut ® C18 ® manufactured by Analytichem International. Silica gel coated with octylsilane is also a suitable adsorbent in the process of the invention. Organic polymeric resins may also be used in the practice of the invention. These resins include rigid, macroreticular styrene-divinylbenzene copolymer resins having adsorptive properties similar to the above materials, such as PRP-1 ® manufactured by Hamilton Company.

The adsorbents may be packed into a column but are preferably used in the form of small cartridges fitted with a syringe. The most preferred adsorbent for use in the process of the invention is the Sep-Pak ® C18 adsorbent in an adsorbent cartridge.

Prior to passing the pretreated isothiazolone-containing aqueous sample through the adsorbent, it is desirable to condition the adsorbent as by properly wetting the adsorbent. This conditioning may be conducted by treating the adsorbent with a 50:50 (volume) percent solution of acetonitrile in deionized water followed by a 0.0001N sodium hydroxide solution rinse. The pH of the sodium hydroxide rinse solution (deionized water) being about the same as the pH of the pretreated sample.

The best technique for conducting the adsorption is by attaching the top of the adsorbent cartridge to the fitting of a three way syringe valve connected to a 30 cc Luer-Lock ® syringe. The sample is then fed downflow through the syringe, through the valve and through the adsorbent cartridge. The technique of using the three way syringe is described in detail in U.S. Pat. No. 4,514,504 as it relates to its use for the adsorption and concentration of polyacrylic acids in aqueous systems. The top of the syringe may be fitted with a plunger to force the sample through the adsorbent at a uniform rate of about 10 milliliters per minute. Subatmospheric pressure (vacuum) can also be applied to force the sample through the adsorbent. The water, hardness ions, other biocides and interfering compounds not removed by the pretreatment step are not adsorbed onto the adsorbent and exit the adsorbent as effluent.

The adsorbed, pretreated isothiazolones are, therefore, selectively concentrated on the adsorbent. The volume of the sample which passes through the adsorbent is typically constant so that the concentration of the isothiazolones in the aqueous sample can be determined. By increasing the volume of sample fed to the adsorbent, the sensitivity of the concentration measurement of the isothiazolones in the sample can be further increased. The adsorbent is then typically rinsed with 0.0001N sodium hydroxide solution (pH 10) to displace any interstitially trapped sample.

The adsorbed, pretreated, isothiazolones are then desorbed from the adsorbent by the use of a suitable displacement fluid which completely displaces adsorbed isothiazolones and does not interfere with the ability of the adsorbent to be reused or with the subsequent color complexing reaction. When the displacement fluid is added to the syringe, the valve should be closed to the cartridge and the plunger removed. When the valve is not attached, the adsorbent cartridge should first be removed to prevent disturbance of the adsorbent. The three-way Luer-Lock ® valve, is perferably used in the practice of this invention, allows for variety of operations. One position of the valve is closed to the cartridge and the air. When the valve effluent pathway is positioned in the direction of liquid flow through the syringe, the liquid passes directly through the cartridge. This position is used during conditioning, adsorption, and desorption. When the valve effluent pathway is positioned in a direction perpendicular to flow through the syringe, the syringe effluent pathway is to air. This position allows for the removal of the syringe plunger without disturbing or removing the cartridge. This valve position also allows for drawing a reagent up into the syringe for subsequent passage through the cartridge without removal of the plunger. When the three-way valve is not connected to the syringe, the cartridge must be removed before the syringe plunger is pulled back to allow for the addition of additional fluid. After the plunger is removed, the cartridge may then be replaced and the displacement fluid is pushed through the adsorbent with the reinserted plunger.

Aqueous solutions of water-miscible organic solvents such as acetonitrile or methanol may be used to desorb the adsorbed isothiazolone. Desorbing the isothiazolones using a 50:50 acetonitrile solution, as used in the adsorbent conditioning step, is preferred.

We have found that the sensitivity of the method can be further improved by using two cartridges in series rather than one. Whether one or multiple cartridges are used in the method, the final results of the method should not be significantly different provided that the calibration curve used for comparison is based on the use of the same number of cartridges. The adsorbent can be reused after isothiazolones are desorbed by rinsing the adsorbent after desorption with a solution of 0.0001N sodium hydroxide.

The desorbed isothiazolone solution is collected and the ring structure of the isothiazolones is broken by the addition of a base such as, for example, a 2N solution of sodium hydroxide in theory according to the following mechanism:

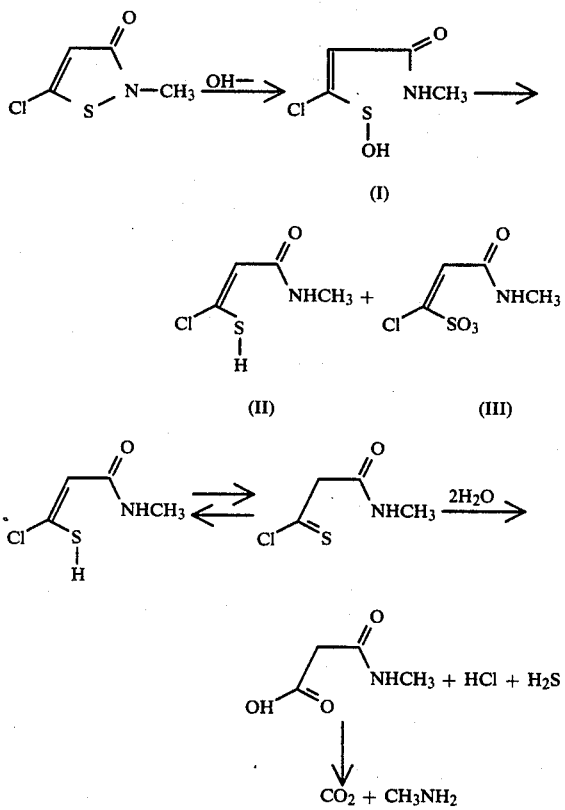

Following the breaking of the isothiazolone ring, potassium ferricyanide and ferric chloride are added to the desorbed sample to form a blue complex. Four drops of 1% potassium ferricyanide (4 micromoles) were added to the sample containing the broken isothiazolones, followed by the addition of a stochiometric excess of 2 milliliters of 0.2% acidified ferric chloride (15 micromoles). The acid, which we have found to be preferably added with the ferric chloride, can be added in a separate step, but incorporation of the acid with the ferric chloride stabilizes the solution for long term storage, preventing the formation of the insoluble hydroxide. The acid also serves to neutralize the base that was added to cleave the ring and enables the reaction to proceed under acidic conditions. The resultant "blue" solution appears to be a colloidal suspension of soluble and insoluble Prussian or Turnbull's blue. The exact chemical composition of the complex is unclear since mixed oxidation state complexes of soluble and insoluble Prussian blue and Turnbull's blue have been reported in the literature when these reagents are used for color complex reactions. Although the reaction is reported as the "Prussian blue reaction", it is believed that the ferric (III) ion is being reduced to ferrous (II) by the cleaved isothiazolone with subsequent reaction with ferricyanide forming Turnbull's blue. Regardless of the exact mechanism and composition of the color complex, the resulting blue color produces highly sensitive colorimetric results. When the concentration of the isothiazolones in the aqueous samples is on the order of 0.25 to 3 ppm, the color complex is closer to a green color than to a blue color (referred to herein as "blue" for simplicity).

Following the formation of the "blue" complex the concentration of the isothiazolones in the aqueous system can be determined using colorimetric methods. The easiest method is by visual inspection and comparison of the color complex with standards of known concentration. Another method is to utilize a colorimeter, such as a Hach DR/1A colorimeter, to measure the percent light transmission through the color complex sample at a wavelength of about 610 nanometers. The percent transmittance is then converted to the isothiazolone concentration from a previously prepared concentration calibration curve.

We have found that this colorimetric method is highly sensitive to low concentrations of isothiazolones in commercial cooling tower waters. The composition of a typical cooling tower water is presented in Table 2.

TABLE 2

| Analysis of Typical Cooling Tower Water | |
|---|---|
| Total Mg | 93 ppm |
| Total Ca | 565 ppm |
| Total Fe | 0.46 ppm |
| Soluble Zn | 1 ppm |
| Na | 155 ppm |
| Chromate | 14 ppm |
| Chromium | 1.2 ppm |
| Sulfite & Sulfate | 285 ppm |
| Choride | 230 ppm |
| Total Hardness (as $CaCO_3$) | 660 ppm |
| Silica | 37 ppm |
| Total Phospate | 6 ppm |
| Inorganic Phosphate | 4 ppm |
| Orthophosphate | 3 ppm |
| Copper | 0.05 ppm |
| Conductivity | 1659 micromhos |
| pH | 8.1 |

The following presents a description of the general procedure with the method of the invention.

We transferred 20 milliliters of an aqueous sample containing isothiazolones including Kathon ® 886 to a plastic beaker to which we added two drops of 2N sodium hydroxide. We then filtered the aqueous sample through a 5 micrometer Acrodisc ® filter into another plastic beaker.

We then conditioned the SEP-PAK $C_{18}$ ® adsorbent cartridge(s) as follows: when one cartridge was used we rinsed the cartridge with 5 milliliters of a 50/50 acetonitrile/water solution followed by a rinse using 5 milliliters of a 0.0001N sodium hydroxide in deionized water; when two cartridges in series were used, we rinsed the cartridges with 20 milliliters of 0.0001N sodium hydroxide in deionized water after the acetonitrile/water treatment.

We then drew the filtered sample up into a 30 milliliter disposable syringe fitted with a 3-way valve and pushed the solution slowly at a rate of 10 milliliters/minute through the conditioned adsorbent cartridge(s). We then rinsed the adsorbent with 10 milliliters of 0.0001N sodium hydroxide in deionized water and displaced the adsorbed isothiazolones from the adsorbent using 10 milliliters of a 50/50 acetonitrile/water solution. The eluent was then diluted to 25 milliliters using deionized water. We then added 1.0 milliliter of 2N sodium hydroxide in deionized water to the diluted eluent. We then waited for two minutes before adding four drops (about 130 microliters) of one weight percent postassium ferricyanide in deionized water (1 gram per 100 ml water). After waiting an additional minute we then added 4 drops of a 2% ferric chloride solution in deionized water (2 grams in 100 ml water) and waited another minute before adding 20 milliliters of 2N hydrochloric acid in deionized water. We then waited 10 minutes before conducting the colorimetric analysis. Subsequently, we have found it preferable to add 2 milliliters of a 2% ferric chloride solution in a 2N hydrochloric acid (0.2 grams in 100 ml 2N HCl), and thereby combining these steps we have improved the ferric chloride stability without changing the results.

We used a Hach DR/1A colorimeter and measured the percent light transmitted through the complexed solution at 610 nanometers. We then converted the % transmittance to a concentration utilizing the calibration curve previously prepared, as presented in Table 3.

TABLE 3

| Kathon ® Calibration Curve | | |
|---|---|---|
| Sample | % T | Absorbance |
| Blank | — | 0.0 |
| 0.125 ppm | 100 | 0.0 |
| 0.25 ppm | 95 | 0.022 |
| 0.50 ppm | 92 | 0.036 |
| 1.0 ppm | 88 | 0.056 |
| 2.0 ppm | 79 | 0.102 |
| 5.0 ppm | 63 | 0.200 |
| 7.5 ppm | 54 | 0.268 |
| 10.0 ppm | 46 | 0.337 |

As seen from Table 3, the slope of the % absorbance (transmission) versus isothiazolones (Kathon ® 886) concentration curve is very high at low concentrations, indicating a high degree of sensitivity for this method at concentrations as low as about 0.1 ppm.

This technique was used with a number of cooling tower waters and the results were compared with high pressure liquid chromatograph results.

Table 4 shows the results of the method when two SEP-PAK $C_{18}$ ® cartridges were used instead of one SEP-PAK $C_{18}$ ® with a solution of known isothiazolone concentration. The charge fraction and the rinse fraction were analyzed to determine breakthrough and retention of isothiazolone on the cartridge(s). The charge fraction is the liquid that exits the cartridge(s) after the sample solution containing 1 ppm isothiazolone was pushed through the cartridge(s). The rinse fraction is the liquid that exits the cartridge(s) after rinsing the cartridge(s) with the dilute sodium hydroxide solution. If the method is working optimally the cartridge(s) adsorbs all the isothiazolones and no isothiazolone should be detected in either the charge fraction or rinse fraction (no break through). A color test was conducted on each charge fraction but essentially no color was observed indicating no significant isothiazolone breakthrough. This observation was confirmed by HPLC.

TABLE 4

| | Breakthrough Study | |
|---|---|---|
| No. of | HPLC Result (ppm) | |
| Cartridges | Charge | Rinse |
| 1 | 0.1 | <0.1 |
| 2 | 0.1 | <0.1 |

The ability of the pretreatment and adsorption steps to remove interfering materials is illustrated in Table 5.

TABLE 5

| Interference or Compatibility Tests | | | |
|---|---|---|---|
| ITEM | Level ppm | Interference Yes (Positive (+)) or No (Negative (−))[d] | Interference Eliminated by Pretreatment Yes or No[e] |
| Dequest ® | 19 | Yes(+) | Yes |
| Dequest ® | 20 | No | — |
| Dequest ® | 20 | Yes(+) | Yes |
| Acrysol ® LMN-45 | 11 | No | — |
| STPP[a] | 20 | No | — |
| | 100 | Yes(−) | No |
| calcium hypochlorite[b] | 1 | No | — |
| Hyamine ® 3500 | 5 | No | — |
| TBTO[c] | 5 | No | — |

[a] STPP is sodium tripolyphosphate
[b] as chlorine
[c] TBTO is tributyltinoxide
[d] Color test performed without pretreatment and adsorption steps. Interference test determines whether presence of conventional water treatment chemicals caused interference in colorimetric analysis. This interference could cause results to be higher than actual (Positive (+)) or lower than actual (Negative (−)) concentration present.
[e] This color test was performed with pretreatment and adsorption steps in instances where absence of these steps indicated interference in results. Results indicate whether repetition of experiment using these steps could eliminate the interference.

Dequest 2000

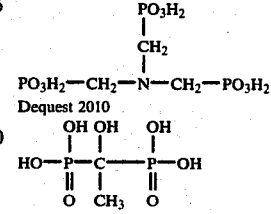

Dequest 2010

$$\begin{array}{c} \text{OH} \;\; \text{OH} \;\;\;\;\;\; \text{OH} \\ | \;\;\;\; | \;\;\;\;\;\;\;\;\; | \\ \text{HO}-\text{P}-\text{C}-\text{P}-\text{OH} \\ || \;\;\;\; | \;\;\;\;\;\;\;\;\; || \\ \text{O} \;\;\; \text{CH}_3 \;\;\;\; \text{O} \end{array}$$

This test demonstrates that various commonly encountered cooling water chemicals yield interferences to the method when no pretreatment and adsorption is used, and that these steps eliminate most interferences present at concentrations typically encountered in aqueous samples.

What is claimed is:

1. A method for determining the concentration of isothiazolones in an aqueous system comprising:
   (a) pretreating a known volume of the aqueous system containing isothiazolones by adjusting the pH of the sample to about 10;
   (b) selectively adsorbing said isothiazolones from the pretreated sample onto a nonpolar adsorbent;
   (c) desorbing said adsorbed isothiazolones from said adsorbent;
   (d) breaking the ring structure of said desorbed isothiazolones by the addition of a base;
   (e) reacting said ring broken isothiazolones with ferric chloride and potassium ferricyanide to form a color complex; and
   (f) colorimetrically determining the concentration of the isothiazolones in said aqueous sample by comparing the color complex with a standard of known concentration.

2. The method of claim 1 where the concentration of said isothiazolones in said aqueous system ranges from about 0.1 parts per million to about 20 parts per million.

3. The method of claim 1 where the nonpolar adsorbent comprises bonded phase silica gel.

4. The method of claim 1 where a solution of acetonitrile and deionized water in equal volumes is used to desorb the adsorbed isothiazolones.

5. The method of claim 1 where the ring structure of the desorbed isothiazolones is broken by the addition of 2N sodium hydroxide.

6. The method of claim 1 where the colorimetric determination is made using a colorimeter at a wavelength of about 610 nanometers.

7. The method of claim 1 where the adsorbent is conditioned before adsorbing the isothiazolones by rinsing the adsorbent with a solution of acetonitrile and deionized water at a pH of about 10.

8. A method for determining concentrations of isothiazolones in an aqueous system of from about 0.1 to about 20 parts per million comprising:
   (a) pretreating a known volume of the aqueous system containing isothiazolones by adjusting the pH of the sample to 10 and filtering the sample through a 5 micron filter;
   (b) selectively adsorbing said isothiazolones from the pretreated sample onto a conditioned nonpolar, bonded phase, silica gel adsorbent;
   (c) desorbing said adsorbed isothiazolones from said adsorbent using a solution of acetonitrile and deionized water;
   (d) breaking the ring structure of the desorbed isothiazolones by adding a 2N solution of sodium hydroxide;
   (e) reacting the ring broken isothiazolones with acidic ferric chloride and potassium ferricyanide to form a blue color complex; and
   (f) colorimetrically determining the concentration of the isothiazolones in said aqueous sample by measuring the amount of 610 nanometer wavelength light transmitted through the blue complex.

* * * * *